United States Patent [19]

Hori et al.

[11] Patent Number: 5,792,712

[45] Date of Patent: Aug. 11, 1998

[54] MICROBICIDAL MAT AND METHODS OF MANUFACTURING AND USING THE SAME

[75] Inventors: Shoji Hori; Satoru Toyoshima; Junichi Yamanaka, all of Sakai; Akira Kawabata, Osaka; Hiroaki Mitsuhashi, Osaka; Yukio Ushiya, Hannan; Masayuki Yamada, Tokyo, all of Japan

[73] Assignee: Daiken Iki Co., Ltd., Osaka, Japan

[21] Appl. No.: 737,932

[22] PCT Filed: Apr. 1, 1996

[86] PCT No.: PCT/JP96/00902

§ 371 Date: Dec. 3, 1996

§ 102(e) Date: Dec. 3, 1996

[87] PCT Pub. No.: WO96/31153

PCT Pub. Date: Oct. 10, 1996

[30] Foreign Application Priority Data

Apr. 4, 1995 [JP] Japan ................................. 7-079099
Sep. 26, 1995 [JP] Japan ................................. 7-011075 U

[51] Int. Cl.$^6$ .................... A47L 23/22; A01N 59/00; A61L 2/16
[52] U.S. Cl. .................... 442/123; 15/104.93; 15/215; 15/217; 428/96; 442/63
[58] Field of Search .................... 15/104.93, 215, 15/217; 428/96; 442/123, 63

[56] References Cited

U.S. PATENT DOCUMENTS

| | | | |
|---|---|---|---|
| 3,956,155 | 5/1976 | Schwuger | 15/104.93 X |
| 4,837,079 | 6/1989 | Quantrille et al. | 15/104.93 X |
| 5,006,267 | 4/1991 | Vaughn et al. | 210/755 |
| 5,091,102 | 2/1992 | Sheridan | 15/104.93 |
| 5,506,040 | 4/1996 | Cordani | 15/215 X |

FOREIGN PATENT DOCUMENTS

| | | |
|---|---|---|
| 2 206 414 | 8/1973 | Germany. |
| 60-234633 | 11/1985 | Japan. |
| 5-86232 | 12/1993 | Japan. |
| 47057/1992 | 3/1994 | Japan. |
| 3023153 | 1/1996 | Japan. |

OTHER PUBLICATIONS

By Japan Society of Antiblastic and Antifungal Technology "Antiblastic and Antifungal Handbook", May 25, 1986, Gihodo Shuppan Co., Ltd. pp. 448–453.

Ichiro Nishi and two others "Surfactant Handbook", Jul. 5, 1960, Sangyo Tosho Co., Ltd. pp. 738–747.

*Primary Examiner*—Daniel Zirker
*Attorney, Agent, or Firm*—Oblon, Spivak, McClelland, Maier & Neustadt, P.C.

[57] ABSTRACT

The present invention relates to a microbiocidal mat to be installed at the entrance of a clean zone in a biochemical plant, a hospital or a like facility, the mat comprising a mat body 1 containing an alkaline compound 5 as a microbicide. The mat body may further contain a surface active agent and/or a water-retentive agent, the water-retentive agent comprising a substance which is stable against water and has deliquescence. Where the mat body 1 contains the compound and the agents in powdery crystallized states, the mat body 1 is used in a wet state by supplying water thereto after the mat is installed at the entrance. When the mat body 1 is supplied with water, the alkaline compound is dissolved in water within the mat body 1 so that the mat body 1 is imparted with microbiocidal activity. A method of manufacturing such a mat comprises the steps of: impregnating the mat body 1 with an aqueous solution of the contained substances, and drying the mat body 1 to cause the contained substances to crystallize in the mat body 1.

22 Claims, 8 Drawing Sheets

MICROBICIDAL MAT AND METHODS OF MANUFACTURING AND USING THE SAME

TECHNICAL FIELD

The present invention relates to microbicidal mats for use in preventing various microbes from being brought into clean zones of semiconductor plants, biochemical plants, hospitals, old-aged homes or like facilities by persons entering the clean zones.

BACKGROUND ART

Microbicidal mats are installed at entrances of rooms in hospitals for preventing nosocomial infection and the like due to proliferation of pathogenic bacteria and other microbes adhering to footwear.

Conventional microbicidal mats of this type include, for example, those comprising only a rubber base and a sticky sheet overlying the rubber base, those comprising a rubber base and an overlying cotton cloth impregnated with a disinfectant, and those comprising a cotton cloth impregnated with a disinfectant and adapted to be laid directly on a floor.

Of these, those mats having a mere sticky sheet attempt to eliminate microbes adhering to the bottom of footwear by utilizing the stickiness of the sticky sheet. Such mats, though exhibiting a certain effect on dust, have little microbicidal effect and, therefore, often leave microbes adhering to the sticky sheet alive, thus resulting in mats unsatisfactorily serving as microbicidal mats.

Those mats having a cotton cloth impregnated with a disinfectant, though exhibiting a microbicidal action, are subject to everyday replacement of their cotton cloth because the disinfectant sprayed onto the cloth evaporates in a relatively short time. Such an everyday replacement involves problems of a large consumption of the disinfectant as well as of dangerous and cumbersome operations. Where a cotton cloth is laid directly on a floor, there arises a problem that the disinfectant contaminated by microbes may ooze out onto the floor or corrode the floor.

Thus, there have been proposed microbicidal mats which maintain a microbicidal power over a relatively long time and does not require frequent replenishment of a disinfectant, such mats comprising, instead of a cotton cloth, a water-absorptive polymer sheet or a sponge having a high water retention each impregnated with a disinfectant. With these mats, the use of the water-absorptive polymer sheet or the sponge having a high water retention suppresses the evaporation of the disinfectant.

Typical disinfectants for use in such microbicidal mats include a chlorhexidine gluconate solution and a benzalkonium chloride solution and the like. Recently, there have appeared disinfectant-resistant microbes which have acquired resistance against these disinfectants. Microbicidal mats employing such disinfectants are, therefore, not so successful for preventing infection caused by the disinfectant-resistant microbes.

Although these disinfectants can exhibit a certain degree of anti microbial activity against such disinfectant-resistant microbes if the concentration or amount thereof to be used is increased, the use of a large quantity of a disinfectant is not practical in terms of cost.

Further, although it is desired that these microbicidal mats be disposed of by incineration after having been used for a predetermined period of time for sanitary reason, they often have residual water because of their water-retentive characteristics and hence are difficult to incinerate.

In view of the foregoing, it is an object of the present invention to provide a microbicidal mat exhibiting a microbicidal activity even against those microbes having a resistance against a disinfectant.

Another object of the present invention is to provide a microbicidal mat which readily allows itself to be disposed of by incineration after use.

DISCLOSURE OF INVENTION

The inventors of the present invention have discovered the fact that an aqueous solution of an alkali metal salt exhibits an extensive anti microbial activity and possesses an anti microbial activity even against microbes having a resistance against a disinfectant such as a chlorhexidine gluconate solution, and have accomplished the present invention.

The present invention provides a microbicidal mat comprising a liquid-absorptive mat body containing an alkaline compound as a microbicide.

In this case, the mat body may further contain a surface active agent and/or a water-retentive agent comprising a substance which is stable against water and has deliquescence in addition to the alkaline compound.

Examples of alkaline compounds to be used for the microbicide include an alkali metal carbonate, an alkali metal bicarbonate, an alkali metal borate or an alkali metal phosphate. The surface active agent is preferably an anionic surface active agent.

These substances contained in the mat body are eventually dissolved in water to function individually according to a method of using the mat to be described later. However, when on market, the mat preferably has the mat body dried to a degree such as to contain the foregoing substances recrystallized into crystals (in powdery states) so as to reduce the time and labor for its transportation and facilitate its quality control.

The mat body may comprise a combustible nonwoven fabric, a foamed polymer resin or other water-absorptive material having voids therein. In the case of the mat body comprising a combustible nonwoven fabric, the mat body may be provided on the top surface thereof with fuzzing-preventive portions made of resin in a scattered fashion, so as to prevent fuzzes of the nonwoven fabric from scattering.

In use, the microbicidal mat of the present invention is rendered wet by supplying water to the mat body comprising any material. Preventing the liquid impregnating the mat body from leaking out enables the wet state of the mat body to be maintained for a prolonged period of time, thus leading to a prolonged duration of the microbicidal activity of the mat.

To this end the underside of the mat body is preferably laminated with a waterstop film. Also, from this standpoint, the mat body is preferably disposed within the recess of a frame. Alternatively, where the microbicidal mat is composed of the mat body solely without using a frame, the mat body is provided on its outer peripheral edges with a bank portion made of a hydrophobic synthetic resin for enclosing the mat body.

Where such a mat body is to be directly installed at the entrance of a clean zone or disposed within the recess of a frame, the waterstop sheet is preferably provided on its underside with a sticky layer.

If a sticky layer having a strong stickiness is directly attached to the underside of the waterstop sheet, the sticky material may adhere to hands or clothing of an operator when the mat body is to be installed or the mat body may become difficult to strip off after use. This may sometimes require time and labor for changing the mat body for a new one.

Thus, it is recommended that on the underside of the waterstop sheet be provided a laminate comprising a plurality of release films each coated with sticky material on the top side thereof. It is possible to further provide a sticky layer on the underside of the laminate. Alternatively, a thermoplastic elastomer sheet having stickiness on opposite sides thereof may be provided on the underside of the waterstop film.

The foregoing alkaline compound is contained in the mat body in an amount such that when the compound becomes a wet state by supplying an appropriate amount of water to the mat body, a pH value ranging between 9 and 12 is attained. Where the mat body further contains a surface active agent, the content thereof is set such that the concentration of the surface active agent assumes from 0.1 to 0.5 vol. % when the concentration of the alkaline compound is such that the resulting aqueous solution assumes a pH value ranging between 9 and 12.

The present invention further provides a method of manufacturing a microbicidal mat comprising a mat body containing as a microbicide an alkaline compound in a recrystallized state.

Specifically, the method comprises a first step of impregnating the mat body with an aqueous solution of the alkaline compound serving as a microbicide, and a second step of drying the mat body to cause the contained substance to recrystallize in the mat body.

Where the mat body is desired to further contain a surface active agent and/or a water-retentive agent, the surface active agent and/or the water-retentive agent may be dissolved in the aqueous solution in the first step, and such substances as well as the alkaline compound may be caused to recrystallize in the second step.

The present invention still further provides a method of using a microbicidal mat comprising a mat body containing as a microbicide an alkaline compound in a recrystallized state.

Specifically, the method comprises supplying the mat body with water in an amount such as to attain a pH value of from 9 to 12 and using the mat with the mat body in a wet state.

Where the mat body is desired to further contain a surface active agent in this method, the amount of the surface active agent is set such that when the mat body is supplied with water in an amount such as to attain a pH value of from 9 to 12, the concentration of the surface active agent is from 0.1 to 0.5 vol. %. In this case, the mat body may further contain a water-retentive agent in a crystallized state before the supply of water.

In the microbicidal mat of the present invention the alkaline compound contained in the mat body exhibits extensive anti microbial activity in a wet state even against microbes having acquired a resistance against disinfectants. Therefore, the mat is useful for preventing nosocomial infection.

Where the mat body further contains a surface active agent, the mat exhibits an enhanced immediate microbicidal effect and a prolonged microbicidal duration.

Further, where the mat body further contains a water-retentive agent comprising a substance which is stable against water and has deliquescence, the water-retentive agent catches water vapor contained in the atmosphere and retains it in the mat body, resulting in a prolonged duration of the microbicidal activity.

Such microbicidal activity can be maintained by a mere supply of water and, hence, the microbicidal mat can be used for a predetermined period of time by a mere replenishment of water. This leads to a reduced cost.

BEST MODE FOR CARRYING OUT INVENTION

Embodiments of the present invention will now be described with reference to the drawings.

Figure 1:
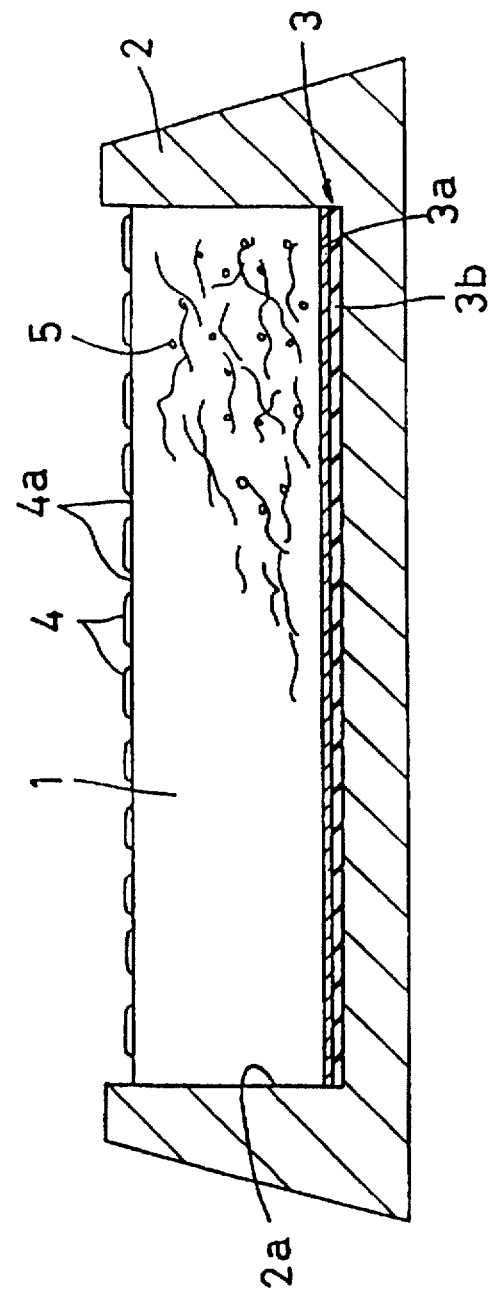
FIG. 1 is a sectional view showing an example of a microbicidal mat having a frame.

Referring to FIG. 1, numeral 1 denotes a mat body fitted in recess 2a of a frame 2. A sticky portion 3 is provided on the underside of the mat body 1 to allow the mat body 1 to be removably attached to the frame 2.

Examples of materials usable for the mat body 1 include woven and nonwoven fabrics made of natural fibers such as cotton, flax and cellulose fiber or of synthetic fibers such as polyester fiber, nylon fiber, acrylic fiber and polypropylene fiber, and other cloth materials. The present invention uses thick ones of these cloth materials having, for example, a METSUKE of 50 to 300 $g/m^2$. Preferably used as such cloth materials are sponge cloths of nonwood pulp, for example, CHAFFLOSE SPONGE CLOTH.

The material of the mat body 1 may be a foamed polymer. Examples of specific foamed polymers include foamed materials such as made of cellulose, polyethylene, polystyrene, polyacrylonitrile, polyvinyl chloride, rubber and synthetic rubber. Particularly preferable among these materials are foamed materials of cellulose, polyvinyl alcohol and polyetherurethane in terms of their good wear resistance and high water absorption property. Those foamed polymers having thicknesses of from about 1 to about 10 mm can be suitably used.

Besides the foregoing materials, the mat body 1 may be composed of a sponge or knitted material. When the convenience for incineration after use is taken into account, the mat body 1 is preferably formed of a combustible nonwoven fabric. Such a combustible nonwoven fabric is made of, for example, natural fiber such as cotton or flax, regenerated fiber such as made of rayon, and combustible synthetic fiber such as polyester fiber or acrylic fiber.

Where the mat body 1 is formed of a nonwoven fabric, the mat body 1 is preferably provided with fuzzing-preventive portions 4 of resin arranged in a scattered fashion on the top surface of the mat body 1 for preventing scattering of fuzzes of the nonwoven fabric. The fuzzing-preventive portions 4 are preferably formed of an acrylic resin affording an achromatic transparent coating film. Such fuzzing-preventive portions 4 can be easily formed by, for example, spraying onto the top surface of the mat body 1 a liquid coating of resin which is curable at room temperature.

The mat body 1 contains powdery crystal of an alkaline compound 5 substantially uniformly as a microbicide. This alkaline compound may be any compound exhibiting alkalinity when in an aqueous solution state, without any particular limitation on the species thereof. Examples of specific alkaline compounds include hydroxides of metals such as sodium hydroxide and potassium hydroxide, and salts of alkali metals and weak acids. Of these, salts of alkali metals and weak acids are preferably used in terms of their easy handling and safety.

Examples of such salts include carbonates such as lithium carbonate, sodium carbonate and potassium carbonate; bicarbonates such as lithium bicarbonate, sodium bicarbonate and potassium bicarbonate; borates such as lithium borate, sodium borate and potassium borate; and hydrogen phosphates such as disodium hydrogen phosphate, dipotassium hydrogen phosphate and dilithium hydrogen phosphate.

Preferably, the mat body 1 contains in addition to the alkaline compound a surface active agent in a crystallized state (not shown), since the combination of the alkaline compound and the surface active agent will provide an immediate microbicidal effect.

Conceivably, the mat body 1 may contain only the surface active agent, and there have conventionally been used mats of the type comprising a cotton cloth or the like impregnated with a surface active agent as a disinfectant.

Although disinfectants including surface active agents, in general, exhibit an immediate microbicidal action in several minutes to several ten minutes, this microbicidal action, when in the presence of an organic substances such as bacteria, tends to be conspicuously weakened with lapse of time. Accordingly, the disinfectants cannot maintain their microbicidal action up to the end of the period of service (typically about a week) of the mats at the time of which the used mat has to be replaced with a new one.

The amount of the surface active agent contained in the mat body 1 is preferably such that when the concentration of the alkaline compound in an aqueous solution is such as to attain a pH value of from 9 to 12, the concentration of the surface active agent in the aqueous solution is from 0.1 to 0.5 vol. % on a stock solution basis. This is because if the concentration of the surface active agent is lower than 0.1 vol. %, the outstanding effect which would result from the combination of the alkaline compound with the surface active agent is not observed.

On the other hand, the reason why the upper limit of the concentration of the surface active agent is set to 0.5 vol. % is that although surface active agents in general become more effective as their concentration grows higher, the mat becomes more expensive inevitably with increasing concentration of surface active agents, in addition to the fact that a necessary and sufficient effect is ensured even when the concentration of the surface active agent is as low as 0.1 to 0.2 vol. % (usual concentration of a disinfectant for floor).

Examples of specific surface active agents include cationic surface active agents such as quaternary ammonium salts and alkylpyridinium salts; anionic surface active agents such as sulfonates and sulfates; ether-type and ester-type nonionic surface active agents; ampholytic surface active agents such as amino acid derivatives and betaine; and polymeric surface active agents.

Of these, preferred are anionic surface active agents, which are stable in alkaline conditions. The term "anionic surface active agent" used herein means a surface active agent which will exist in the form of anion in an aqueous solution, and includes ampholytic surface active agents. It is possible to use two or more surface active agents in combination, one of which is an anionic surface active agent.

The mat body 1 preferably further contains in addition to the alkaline compound with or without the surface active agent a water-retentive agent (not shown) comprising a substance which is stable against water and has deliquescence.

The term "deliquescence" herein used means a phenomenon that a solid substance catches water vapor in the atmosphere and is dissolved in water thus caught. Examples of specific substances which are stable against water and have deliquescence include calcium chloride, magnesium chloride, strontium chloride, zinc chloride, nickel chloride, cobalt chloride, calcium bromide, zinc bromide and zinc iodide.

Of these, calcium chloride and like materials are well known to have deliquescence utilized in a so-called "dehumidifying product" for domestic use aiming at preventing the proliferation of fungi or at deodoring. By utilizing the deliquescence of such substances, the mat body 1, per se, takes in moisture contained in the air thereby enhancing the moisture retention of the mat. This allows the mat to have a prolonged microbicidal duration and minimizes the number of times of water replenishment to the mat body 1.

While the shape and material of the frame 2 shown in FIG. 1 are not particularly limited, the frame 2 is preferably formed of a rubber or a synthetic resin each having a water resistance and a chemical resistance.

Figure 2:
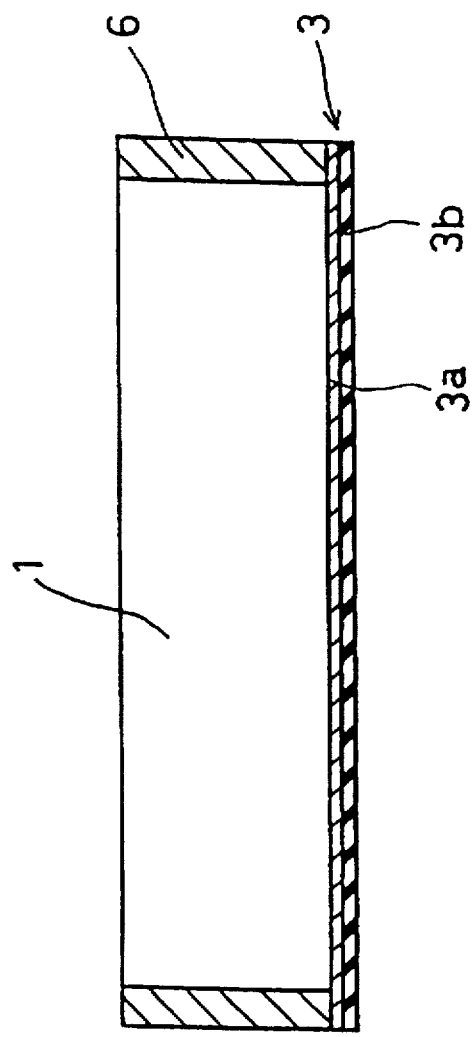
FIG. 2 is a sectional view showing an example of a frameless microbicidal mat.
Figure 3A:
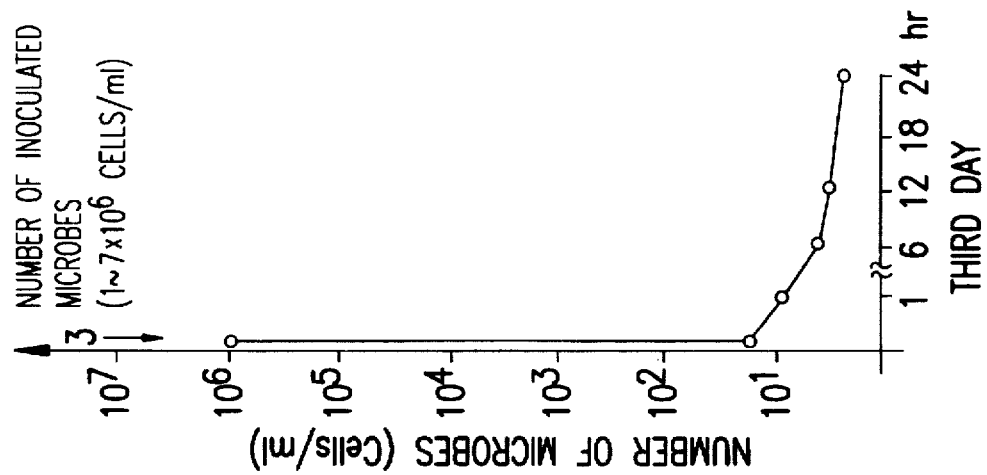
FIG. 3 is a graph for explaining the effect of using a surface active agent and an alkaline compound in combination.
Figure 3B:
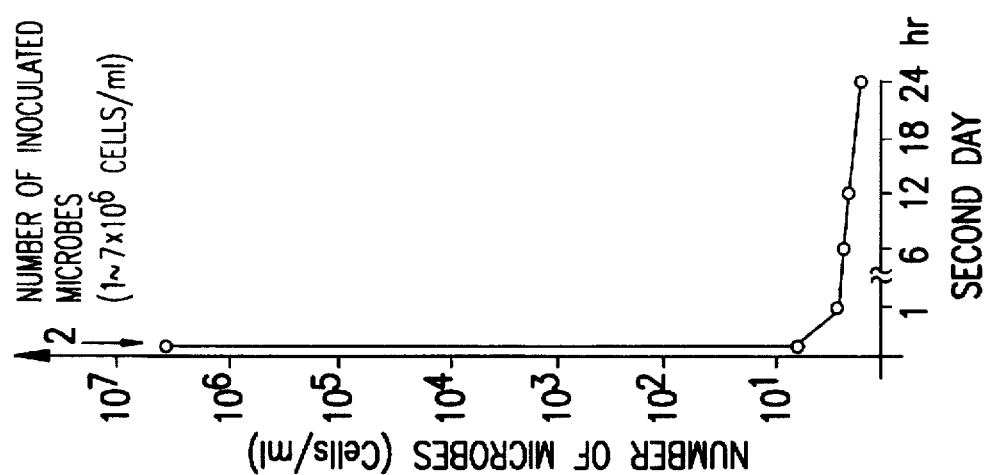
Figure 3C:
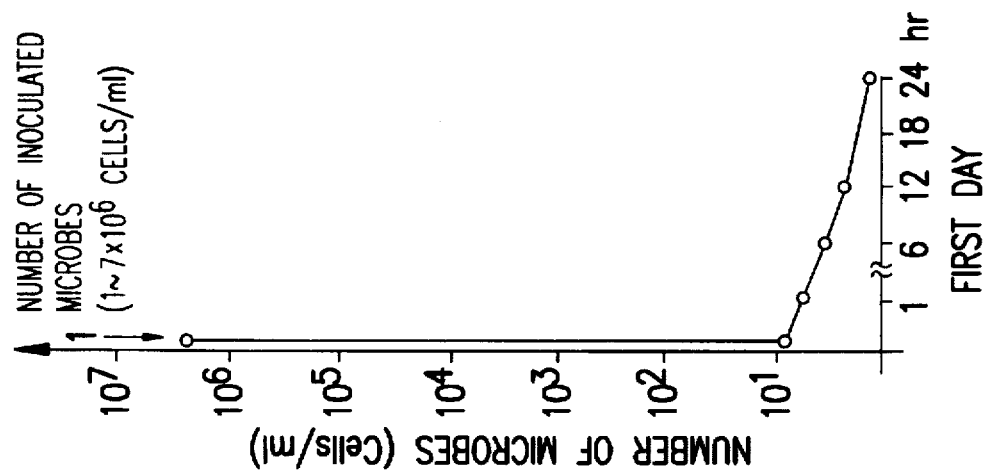
Figure 3F:
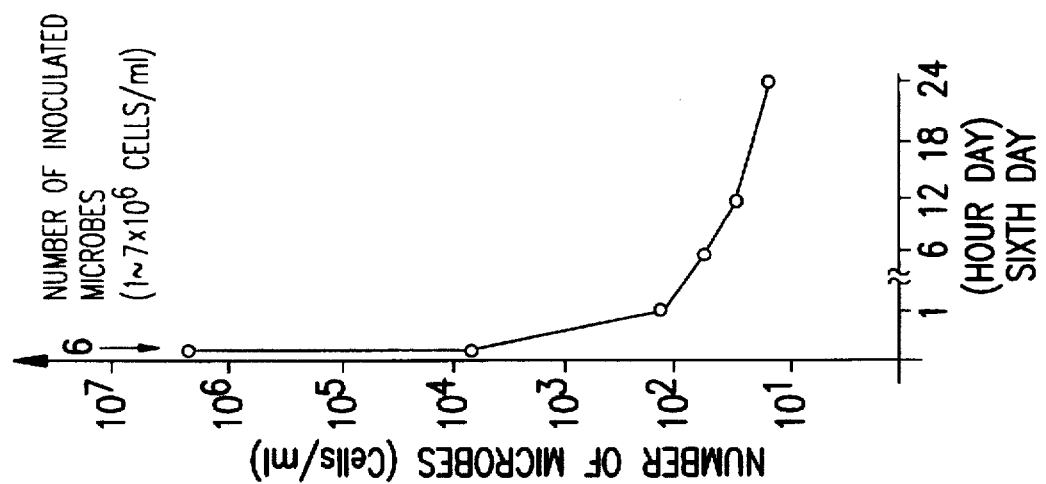
Figure 3E:
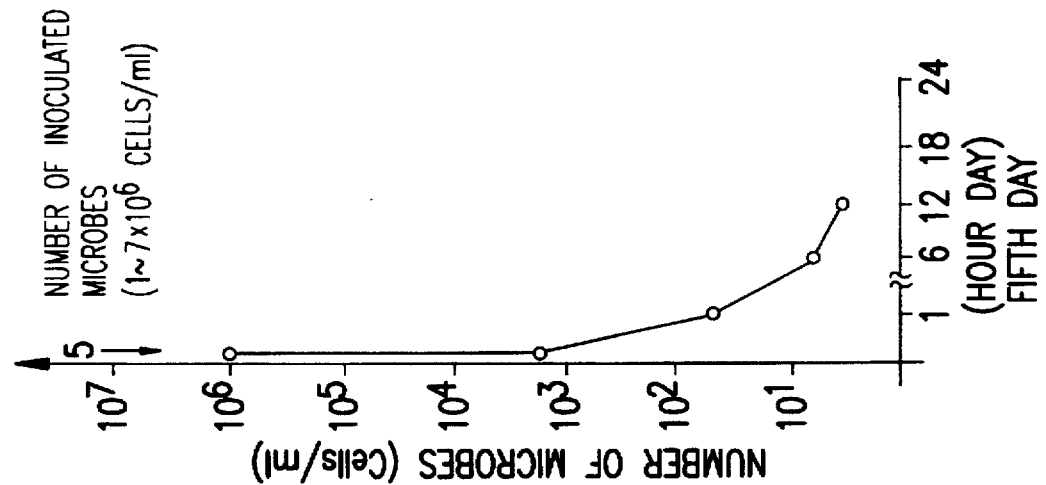
Figure 3D:
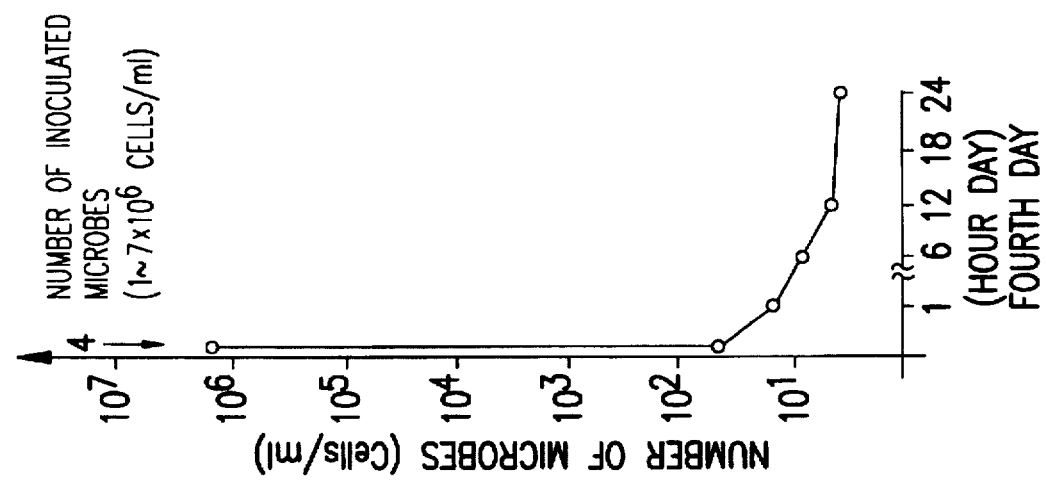
Figure 4C:
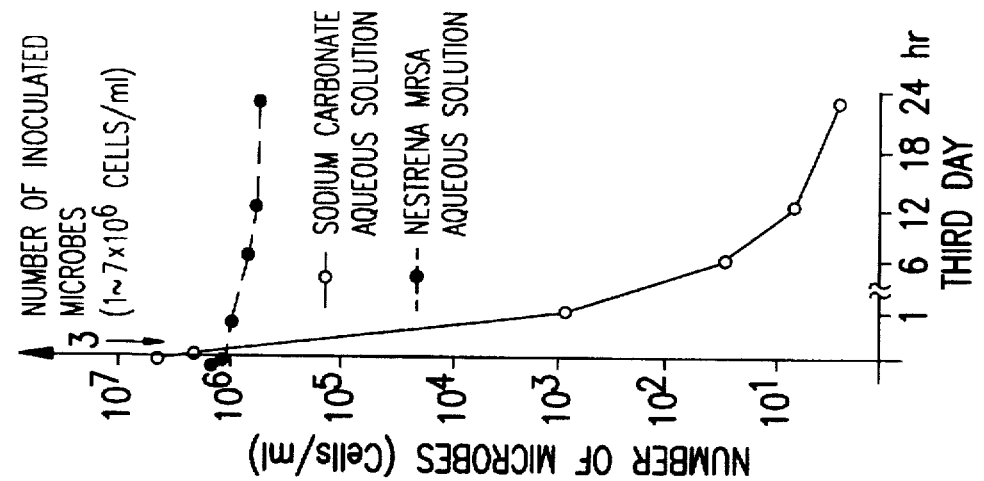
FIG. 4 is a graph of comparative examples for explaining the effect of using a surface active agent and an alkaline compound in combination.
Figure 4B:
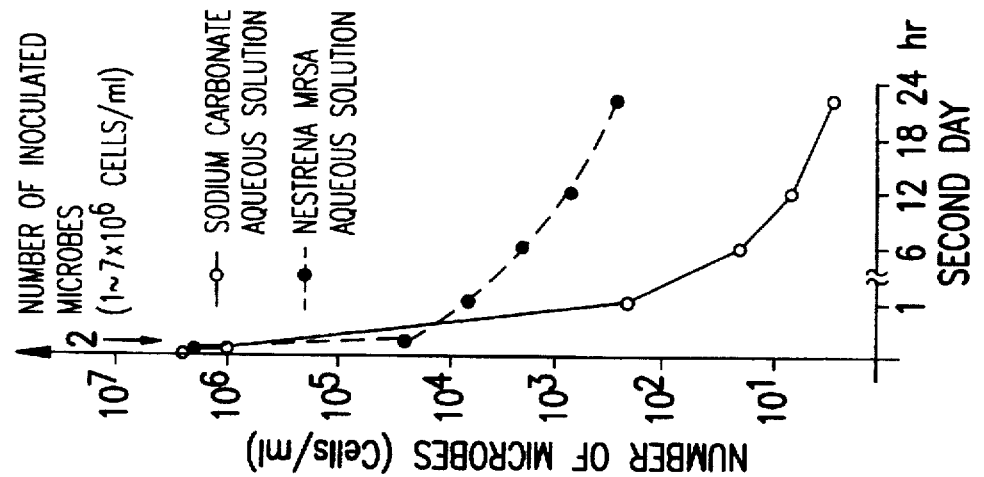
Figure 4A:
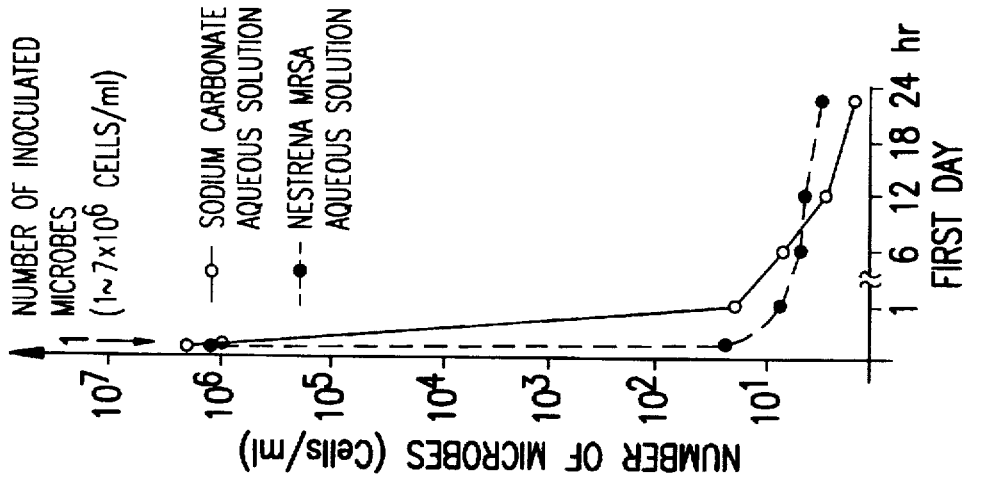
Figure 4F:
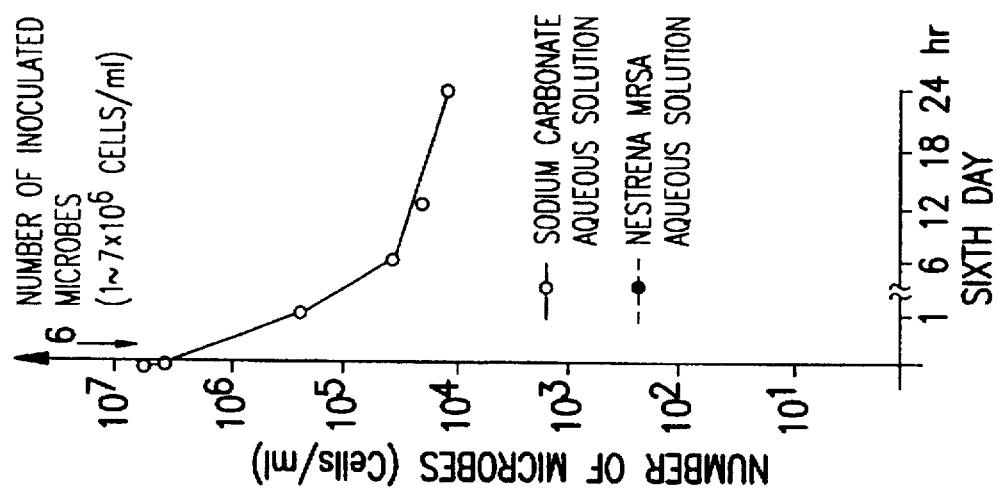
Figure 4E:
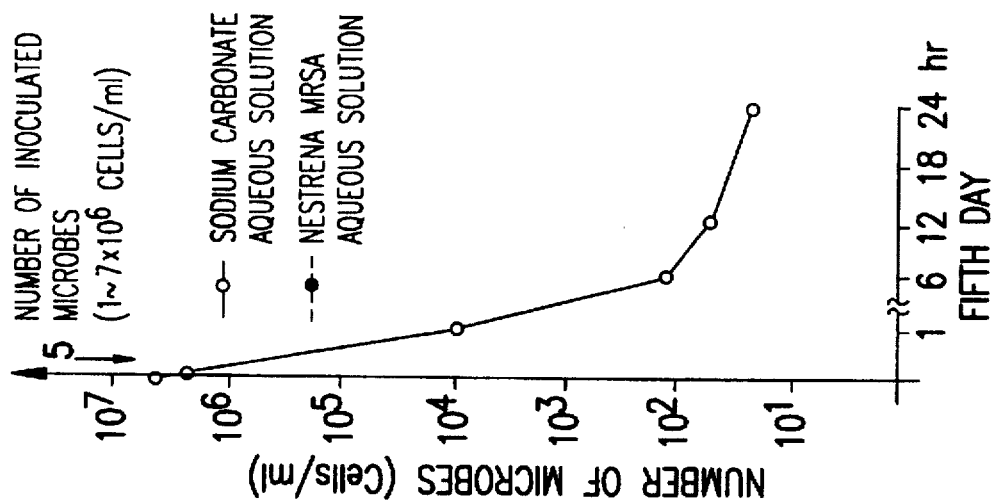
Figure 4D:
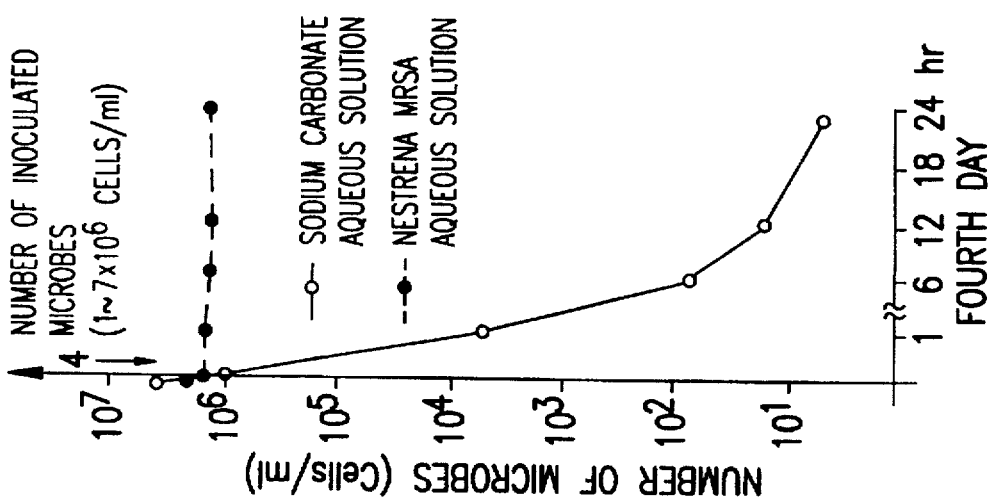

The sticky portion 3 may be formed by directly coating the underside of the mat body 1 with a sticky material. Otherwise, the sticky portion 3 may be formed of a laminate film in which a waterstop film 3a such as made of polyvinyl chloride, polyethylene or polypropylene is laminated with a sticky material 3b as shown in FIGS. 1 and 2 or of a double-coated adhesive tape or the like.

It should be noted that FIG. 1 illustrates the case where the sticky portion 3 is formed of a laminate film comprising the waterstop film 3a and the sticky material 3b and is laminated on the underside of the mat body 1.

The provision of such waterstop film 3a on the underside of the mat body 1 makes it possible to prevent water in the mat body 1 to flow out toward the frame 2 side thereby advantageously preventing deterioration in the stickiness of the sticky material 3b.

Where the mat is so constructed that the mat body 1 will not be shifted or peeled within the recess 2a of the frame 2 by providing, for example, sticky portion 3 or shiftpreventive projections in the recess 2a, the mat body 1 need not necessarily be provided with sticky portion 3. Further, the mat body 1, though comprising a single mat body fitted in the frame 2 according to the foregoing embodiment, may comprise a plurality of stacked mat bodies.

Although the microbicidal mat shown in FIG. 1 has the frame 2, the present invention is not limited to such construction. For example, where the mat body 1 is to be directly affixed to the floor of a building, the microbicidal mat may comprise the mat body 1 solely. In the case of the mat without frame 2, the mat body 1 is preferably provided with a bank portion 6 having a hydrophobic property which encloses the outer peripheral edges of the mat body 1. The height of the bank portion 6 is sized substantially equal to the thickness of the mat body 1.

When the mat body 1 in a wet state is trod, the bank portion 6 prevents the alkaline aqueous solution (optionally containing a surface active agent) from leaking out of the periphery of the mat body 1. In this case the provision of the waterstop sheet 3a on the underside of the mat body 1 will cause the aqueous solution to move toward the top surface of the mat body 1 when the mat body 1 is trod.

For this reason it is possible to maintain the mat body 1 in a wet state for a relatively long time thereby providing economical merits, and at the same time to prevent the floor from getting wet or smudged by the solution which would otherwise leak from the mat body 1 thereby providing sanitary merits.

Where the mat body 1 is fixed by means of the sticky material 3b, the waterstop sheet 3a also prevents the solution from penetrating into the sticky material 3b. Preventing the alkaline solution and/or the surface active agent from penetrating into the sticky portion 3 leads to prevention of a deterioration in the stickiness of the sticky material 3b due to chemical actions of the solution.

The bank portion 6 is preferably formed of a synthetic resin, such as an acrylic resin, polyurethane resin or polyvinyl chloride, which has a hydrophobic property and is possible to easily restore its original shape. Further, the foregoing hydrophobic resin may be used in combination with a fluoroplastic so as to impart the bank portion 6 with water repellency. Although the method of forming the bank portion 6 is not particularly limited, the bank portion 6 can be easily formed by, for example, the following method.

A base resin such as an acrylic resin is admixed with, as required, a fluoroplastic, a tackifier, a crosslinking agent and the like to prepare a resin emulsion, which is optionally diluted with an appropriate organic solvent to prepare a resin solution. The resin emulsion or solution is then applied onto the periphery of the mat body 1, followed by drying (with optional heating) to form the bank portion 6. Like the sticky portion 3, the bank portion 6 of a synthetic resin can be readily formed by coating a continuous raw mat body fabric with the resin emulsion or resin solution using a coater and then cutting the coated fabric into individual mat bodies.

By thus forming the mat body 1 integrally with the highly restorable bank portion 6 the resulting microbicidal mat not only prevents leakage of the aqueous solution contained therein but also enjoys advantages over the microbicidal mat comprising the frame 2 and the mat body 1 fitted in the frame 2.

Specifically, since the mat body 1 and the highly restorable bank portion 6 have the same height, the microbicidal mat will not interfere with the passage of a hand truck with casters thereby contributing to the safety in transporting patients, dangerous chemicals and the like. Further, since expensive frame 2 is dispensed with, it is possible to realize a microbicidal mat with a reduced price and to subject the whole mat to disposal (incineration), thus offering more sanitary merits than the case of repeated use of the frame 2.

It should be noted that the mat with the bank portion 6 is applicable not only to the mat body 1 impregnated with the alkaline compound according to the present invention but also to wet mats impregnated with any liquid other than the alkaline compound in general.

Specifically, as far as a mat to be used in a wet state as having mat body 1 impregnated with a liquid is concerned, the provision of the bank portion 6 integral with the mat on the outer periphery thereof will prevent the liquid from leaking from the outer periphery of the mat without the use of a separate member such as the frame 2. Such a mat maintains its wet state for a predetermined period to ensure a potent microbicidal action for a predetermined period while in addition failing to interfere with the passage of a hand truck with casters or the like when used as laid on the floor. Additionally, since it is not necessary for the mat to be used in combination with a separate member such as a frame, the mat offers a wide selection for its shape and size without any substantial increase in the price thereof.

The microbicidal mat thus described can be manufactured by supplying an aqueous solution of the alkaline compound (optionally together with other substances such as a surface active agent) to the mat body 1 to impregnate the mat body 1 with the aqueous solution (first step), and drying the mat body 1 thus impregnated with the aqueous solution to cause the alkaline compound and other substances to crystallize in the mat body 1 (second step).

The aqueous solution of the alkaline compound can readily be supplied to the mat body 1 by, for example, spraying a small amount of the aqueous solution in high concentration onto the mat body 1 or dipping the mat body 1 into the aqueous solution in high concentration.

Where the mat body 1 contains a surface active agent and/or a water-retentive agent in addition to the alkaline compound, it is preferred to supply such agents to the mat body 1 simultaneously with the supply of the alkaline compound. Specifically, it is preferred to dip the mat body 1 into a mixed solution of the alkaline compound, surface active agent and/or water-retentive agent. This is because such a process allows the number of times of necessary dipping operation to be reduced to only once, hence also the number of times of drying operation to follow to be reduced to only once, thus leading to efficient manufacture.

When the mat body 1 composed of a nonwoven fabric, knitted fabric or woven fabric is impregnated with a solution containing the alkaline compound (together with the optional surface active agent) and then subjected to drying, these substances are recrystallized in the mat body 1 and remain in the form of powder adhering around voids in the mat body 1.

To be described next is a method of using the microbicidal mat. The use method according to the present invention will not be basically varied irrespective of whether or not the mat body contains the surface active agent and/or the water-retentive agent.

As described above, the mat body 1 of the microbicidal mat according to the present invention contains therein such substances as the alkaline compound in a crystallized state and, hence, the mat body 1 is in dried condition before use. In use, an appropriate amount of water is supplied to the mat body 1 to make the mat body 1 wet.

As the water to be supplied can be used tap water, deionized water, sterilized water or like water, without particular limitation. Otherwise, a diluted solution of a disinfectant may be used in combination. If the disinfectant is used in combination with the alkaline compound, these agents will synergistically act to ensure enhanced microbicidal effect.

Examples of preferred disinfectants are those which are stable in alkaline conditions, such as benzalkonium chloride, alkyldiaminoethylglycine hydrochloride, Irgasan DP-300, 2,4,5,6-tetrachloroisophthalonitrile, 2-(hydroxymethylamino)ethanol, and glutaric aldehyde.

The amount of water to be supplied to the mat body 1 is such that the resulting alkaline aqueous solution assumes a pH value of from 9 to 12, and is variable depending on the size of the mat body 1, the kind and content of the alkaline compound contained in the mat body 1, and other factors. A microbicidal mat having mat body 1 of 920 mm×780 mm impregnated with about 5 g of sodium carbonate, for example, may be supplied with 500 to 700 ml of water.

Where the mat body 1 is impregnated with the surface active agent, the concentration of the surface active agent in the alkaline aqueous solution is preferably from 0.1 to 0.5 vol. % on a stock solution basis.

The mat body 1 thus rendered wet exhibits alkalinity and an extensive anti microbial activity. As will be described later, the mat body 1 has a microbicidal activity even against those microbes having acquired resistance against microbicides which have recently been in question. Accordingly, disposing the microbicidal mat of the present invention at the en trance of a clean zone of a hospital or the like will make it possible to eliminate or sterilize microbes adhering to the underside of footwear at recessed portions thereof as well as at protruded portions thereof. Where the mat body 1 is impregnated with the surface active agent as well as the alkaline compound, the mat will exhibit a microbicidal activity immediately after it is rendered wet.

Where the fuzzing-preventive portions 4 are provided on the top of the mat body 1, the fuzzing-preventive portions 4 disposed in a scattered fashion allows water to be absorbed by the mat body 1 from gaps 4a between adjacent fuzzing-preventive portions 4, and permits the alkaline aqueous solution contained in the mat body 1 to ooze out of the gaps 4a when the mat body 1 is trod with shoes or the like, thus ensuring a microbicidal effect.

Further, in the case of the microbicidal mat with the frame 2 (refer to FIG. 1) the aqueous solution oozing out of the mat body 1 trod is prevented from leaking from the frame 2. Similarly, in the case of the microbicidal mat with the bank portion 6 (refer to FIG. 2) the aqueous solution is prevented from leaking from the periphery of the mat body 1. These embodiments thus offer sanitary and economical merits.

The foregoing embodiments illustratively provide microbicidal mats which contain the substances (alkaline compound, surface active agent and/or water-retentive agent) in the form of recrystallized powder and are adapted to be used in a wet state by supply of water.

Microbicidal mats in the scope of the present invention, however, are not precluded from being sold or dealt with as they are in a wet state. Where they are sold or dealt with in a wet state, the amount of the alkaline compound to be contained is such as to provide an aqueous solution having a pH value of from about 9 to about 12. Where the surface active agent is additionally contained therein, the amount of the surface active agent to be used is such that the concentration thereof in the resulting aqueous solution assumes from 0.1 to 0.5 vol. % on a stock solution basis.

The method of manufacturing the mat body 1 is not limited to the process of causing the contained substances to recrystallize, and it is possible to introduce such substances in the form of powder into the mat body 1.

Irrespective of whether the mat body 1 is of the dry type requiring supply of water in use or of the wet type which is in a wet state before use, the evaporation rate of water from mat body 1 is generally higher than that from mat body 1 composed of a water-absorptive polymer and, hence, water needs to be supplied every day. If water is supplied properly, the mat body 1 can be used for about a week. Although evaporation continues after supply of water, only water evaporates and the amounts of the contained substances are hardly reduced except for a loss caused by being taken out as adhering to footwear of persons and the like passing the mat body 1. Therefore, proper supply of water enables the pH value of the aqueous solution to be maintained within the range required to ensure a sufficient microbicidal effect. After use, only the mat body 1 with the sticky material removed therefrom may be subjected to disposal.

Mat body 1 a in dry state is generally subjected to incineration for disposal. In the case of mat body 1 composed of a combustible nonwoven fabric, in particular, it can readily be incinerated. In the case of the mat with the frame 2, only the mat body 1 is to be subjected to disposal, while the frame 2 can be reused by fitting a new mat body into the recess 2a of the frame 2.

It should be noted that even if the surface active agent is supplied together with water to mat body 1 impregnated with the alkaline compound without the surface active agent, such a mat body is hardly expected to provide advantages as high as the case where the mat body is previously impregnated with both the alkaline compound and the surface active agent.

This is because (1) where the surface active agent is supplied to the mat body 1 afterward, the surface of the mat body 1 becomes slimier than the case of mat body 1 previously containing the surface active agent, and because (2) though the surface active agent previously contained in the mat body 1 recovers its surface activity if only supplied with water even after having been dried, the surface active agent supplied to the mat body 1 upon use substantially loses its surface activity when dried and, hence, the mat body 1, when intended to be used for about a week, is required to be supplied with the surface active agent together with water day by day, resulting in comparatively high cost. Thus, when the advantages of the combination of the alkaline compound and the surface active agent are desired, it is desired that the surface active agent be previously contained in the mat body.

The microbicidal effects of the alkaline aqueous solution and the surface active agent will now be described. Relation between the concentration of an alkaline aqueous solution and its microbicidal effect In examining the microbicidal effect of the microbicidal mat according to the present invention were used Staphylococcus aureus IFO 12732 and Pseudomonas aeruginosa IFO 3080 as microbes and sodium carbonate as the alkaline compound.

The microbes were added to a sterilized physiologic saline to prepare a microbe suspension of about $10^7$ cells/ml. To 100 ml of this suspension was added sodium carbonate so as to have a final concentration of 1 wt. %, 0.3 wt. % or 0.1 wt. %., then the resulting suspension was allowed to stand over a whole day and night at room temperature (23° to 25° C.). The microbe suspension thus obtained was diluted with a physiologic saline and 0.1 ml of the diluted suspension was applied to a Trypto-Soya Agar plate culture medium (available from Nissui Pharmacy Industry), followed by culturing in an incubator at 37° C. for 48 hours. The number of microbes thus cultured was determined from the number of colonies thus obtained.

A microbe suspension not containing sodium carbonate, as a control, was allowed to stand over a whole day and night, and then the number of microbes was determined in the same manner as above.

The results of the determination are shown in Table 1.

TABLE 1

|  | Staphylococcus aureus | Pseudomonas aeruginosa |
|---|---|---|
| Before treatment | $1.4 \times 10^7$ cells/ml | $2.9 \times 10^7$ cells/ml |
| 0.1 $Na_2CO_3$ treatment | $9.2 \times 10^3$ cells/ml | $1.5 \times 10^4$ cells/ml |
| 0.3% $Na_2CO_3$ treatment | <10 cells/ml | <10 cells/ml |
| 1.0% $Na_2CO_3$ treatment | <10 cells/ml | <10 cells/ml |
| Control | $4.8 \times 10^7$ cells/ml | $9.8 \times 10^6$ cells/ml |

As seen from Table 1, the treatment using $Na_2CO_3$ in an amount of 0.3 to 1.0 % by weight exhibited a significant anti microbial activity.

It should be noted that 1% sodium carbonate aqueous solution, 0.3% sodium carbonate aqueous solution and 0.1% sodium carbonate aqueous solution showed 10.6, 10.0 and 9.7 in pH value, respectively and the physiologic saline showed 6.4 in pH value.

Alternatively, the microbicidal effect of a microbicidal mat was examined in the same manner as above except that potassium carbonate was used instead of sodium carbonate. The results are shown in Table 2.

TABLE 2

|  | pH | Staphylococcus aureus | Pseudomonas aeruginosa |
|---|---|---|---|
| Before treatment | 6.7 | $2.6 \times 10^7$ cells/ml | $5.5 \times 10^7$ cells/ml |
| 0.1% $K_2CO_3$ treatment | 9.8 | $1.6 \times 10^3$ cells/ml | $8.1 \times 10^3$ cells/ml |
| 0.3% $K_2CO_3$ treatment | 10.4 | <10 cells/ml | <10 cells/ml |
| 1.0% $K_2CO_3$ treatment | 11.0 | <10 cells/ml | <10 cells/ml |
| Control | 6.7 | $0.9 \times 10^7$ cells/ml | $9.1 \times 10^6$ cells/ml |

As seen from Table 2, like the sodium carbonate aqueous solution, the potassium carbonate aqueous solution exhibited a potent microbicidal effect.

In general, cell walls and the like of microbes are freely permeable to hydrogen ions and, hence, the hydrogen ion concentration is maintained equilibrium between the inside and outside of a microbe by diffusion. The optimal pH value for microbes ranges between 2.5 and 9 (for example, the optimal pH value for colibacillus is 6.4 to 7.8, for chorela germ 7.8 to 8.4, and for Eumycetes 4.5 to 6.0). Accordingly, when the ambient condition for microbes is maintained at pH 9 to 12, the pH value inside individual microbes also varies to pH 9 to 12. This results in modification of proteins such as enzymes needed for the growth of the microbes, so that the microbes are liable to die out or to become destructible when subjected to an environmental change such as impact and dryness.

Thus, the microbicidal mechanism according to the present invention is interpreted as being based on the modification of proteins of microbes and the like due to a change in hydrogen ion concentration. Therefore, an aqueous solution of a different alkaline compound, when adjusted to assume a pH value of about 9 to about 12, will exhibit an anti microbial activity as potent as above. Further, the microbicidal mechanism based on a change in hydrogen ion concentration according to the present invention has fewer specificities than antibiotics or disinfectants and hence exhibits a wider anti microbial activity. In addition, microbes will hardly acquire the resistance against the alkaline aqueous solution of the present invention.

Anti microbial Effect of a Microbicidal Mat

As an example of the present invention was used a mat body composed of a nonwoven rayon fabric (920 mm×780 mm) and containing about 5 g of sodium carbonate.

The mat body in a dry state was sprayed with 500 ml of a microbe suspension (the final concentration of sodium carbonate was about 1% by weight), and then trod with footwear so as to be wholly and evenly impregnated with the microbe suspension. Note that the microbe suspension was prepared by adding Staphylococcus aureus, disinfectant-resistant Staphylococcus aureus and Pseudomonas aeruginosa to a physiologic saline to $10^7$ cells/ml each.

After the spraying of the microbe suspension, the mat body was allowed to stand for a predetermined period of time (1 hour, 12 hours or 24 hours) at room temperature. The mat body was then cut to obtain a test sample of 100 mm×100 mm, which was in turn further cut into small pieces of about 5 mm×20 mm. The small pieces were each put into a jar, into which was poured 100 ml of a physiologic saline. The jar was stirred at 200 revolutions/min for one hour to remove the microbes from the small piece of the mat body test sample, thus affording a microbe suspension. Note that the pH value of the microbe suspension was adjusted to between 6.5 and 7.5 after the pouring of the physiologic saline. 0.1 ml of the microbe suspension having a pH value thus adjusted was applied to a Trypto-Soya Agar plate culture medium (available from Nissui Pharmacy Industry), which was then cultured in an incubator at 37° C. for 48 hours. The number of microbes was determined from the number of colonies thus obtained.

As a control a mat body composed of a nonwoven fabric and not containing sodium carbonate, which was shaped and sized identically with the above example, was sprayed with 500 ml of a microbe suspension and wholly and evenly impregnated with the microbe suspension, and then allowed to stand for 24 hours. As in the same manner as above, the number of microbes was determined.

The results of the determination are shown in Table 3.

TABLE 3

|  | Microbe A* | Microbe B* | Microbe C* |
|---|---|---|---|
| Before treatment | $1.9 \times 10^7$ cells/ml | $5.6 \times 10^7$ cells/ml | $2.1 \times 10^7$ cells/ml |
| 1 h. after treatment | $3.9 \times 10^2$ cells/ml | $3.1 \times 10^2$ cells/ml | $5.8 \times 10^2$ cells/ml |
| 12 h. after treatment | $6.8 \times 10$ cells/ml | $7.6 \times 10$ cells/ml | $9.2 \times 10$ cells/ml |
| 24 h. after treatment | <10 cells/ml | $4.0 \times 10$ cells/ml | <10 cells/ml |
| Control | $7.8 \times 10^6$ cells/ml | $4.9 \times 10^6$ cells/ml | $9.4 \times 10^5$ cells/ml |

*Microbe A: Staphylococcus aureus
*Microbe B: Disinfectant-resistant Staphylococcus aureus
*Microbe C: Pseudomonas aeruginosa As seen from Table 3, any of the three kinds of microbes in the mat impregnated with sodium carbonate was markedly reduced in number one hour after the treatment and almost died out 24 hours after the treatment. Thus, the mat body of the present invention is found to have exhibited a potent microbicidal effect. It is particularly noteworthy that the number of Staphylococcus aureus having a disinfectant-resistance was also remarkably reduced. Therefore, the mat body is found to have been capable of exhibiting a potent microbicidal effect on microbes having acquired disinfectant resistance as well as on microbes not having disinfectant resistance.

It should be understood that while the number of each kind of microbes in the control test was slightly reduced 24 hours after the microbes had been applied to the mat body as compared to that upon the application to the mat body, this is interpretably because the microbes adhering to the mat could not completely be removed therefrom in the test.

Effect of Combined use of an Alkaline Compound and a Surface Active Agent

In examining the microbicidal effect of the mat of the present invention was used Staphylococcus aureus IFO 12732 as microbes, sodium carbonate as the alkaline compound, and NESTRÉNA MRSA (tradename) produced by OMORI DIANA Industries as the surface active agent. The NESTRÉNA MRSA is a mixture of a detergent JSB-1 mainly comprising a nonionic surface active agent and an amine-based soap as materials, and a surface active agent ODN-1 which is stable in weak-acidic to weak-alkaline conditions.

A stock solution of NESTRÉNA MRSA (0.3 ml) was admixed with 99.7 ml of a 1 wt. % sodium carbonate aqueous solution. The pH value of the mixture solution was 10.5, and the final concentration of the surface active agent was 0.3 vol. %. Microbes were added to the mixture solution to between $1\times10^6$ and $7\times10^6$ cells/ml, and then the number thereof was determined upon lapses of 10 minutes, one hour, six hours, 12 hours and 24 hours. After 24 hours (i.e., on the second day), again microbes were added to the mixture solution to between $1\times10^6$ and $7\times10^6$ cells/ml, and then the number of microbes was determined upon lapses of 10 minutes, one hour, six hours, 12 hours and 24 hours. The same procedure was repeated for six days.

The results of the determination are shown in FIG. 3, in which the ordinate represents the number of microbes (cells/ml) while the abscissa represents hour and day, and in which numbers 1 to 6 respectively represent results of the first to sixth days in this order, with the first day of inoculation corresponding to number 1.

In a comparative example, microbes were added to a 1.0 wt. % sodium carbonate aqueous solution (pH: 10.5) to between $1\times10^6$ and $7\times10^6$ cells/ml, and then the number thereof was determined upon lapses of 10 minutes, one hour, six hours, 12 hours and 24 hours. The same procedure was repeated for six days. In another comparative example, microbes were added to a 0.3 wt. % NESTRÉNA MRSA aqueous solution to between $1\times10^6$ and $7\times10^6$ cells/ml, and then the number thereof was determined upon lapses of 10 minutes, one hour, six hours, 12 hours and 24 hours. The same procedure was repeated for six days.

The results of the determination are shown in FIG. 4, in which: the ordinate represents the number of microbes (cells/ml) while the abscissa represents hour and day; a solid line (—○—) represents a result of the sodium carbonate aqueous solution while a dotted line (———●———) represents a result of the NESTRÉNA MRSA aqueous solution; and numbers 1 to 6 respectively represent results of the first to sixth days in this order, with the first day of inoculation corresponding to number 1.

The results shown in FIGS. 3 and 4 reveal the following facts. In the case of the sole use of the surface active agent, though most of the microbes died out 10 minutes after the inoculation on the first day, the microbicidal effect lowered with lapse of days and was scarcely observed four days later. In the case of the sole use of the sodium carbonate aqueous solution, though a potent microbicidal activity was exhibited for at least five days, it took at least one hour to cause the microbes to mostly die out and the time required for perish the microbes increased with lapse of days.

On the other hand, in the case of the mixture solution of sodium carbonate and NESTRÉNA MRSA, almost all the microbes died out in 10 minutes after the inoculation of the microbes and a sufficient microbicidal effect was observed over six days though the immediate microcidal effect and the continuous microbicidal effect tended to lower with lapse of days.

To be described next is another embodiment of the present invention.

Figure 5:
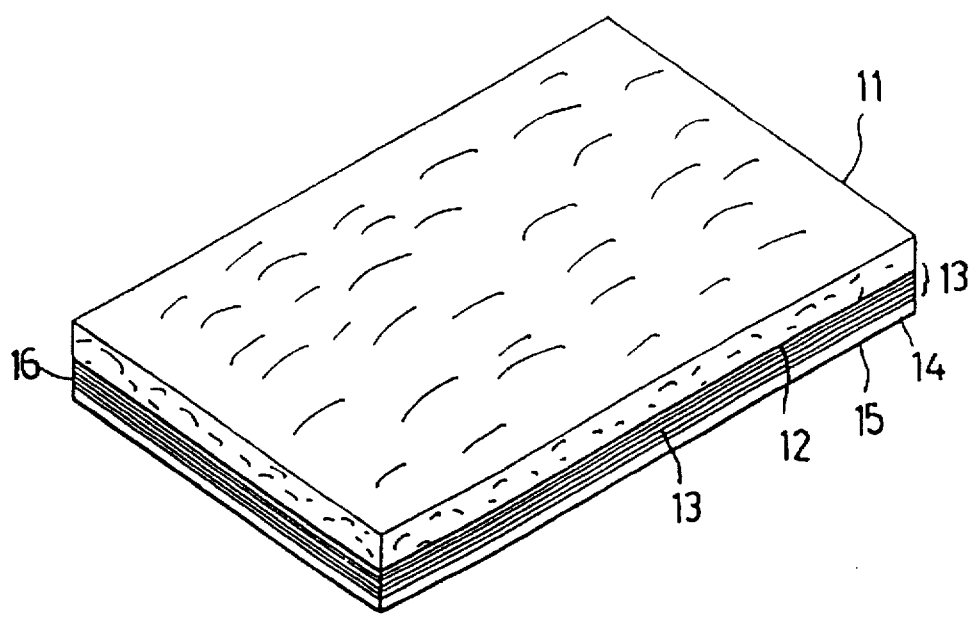
FIG. 5 is a perspective view showing another embodiment of the frameless microbicidal mat.
Figure 6:
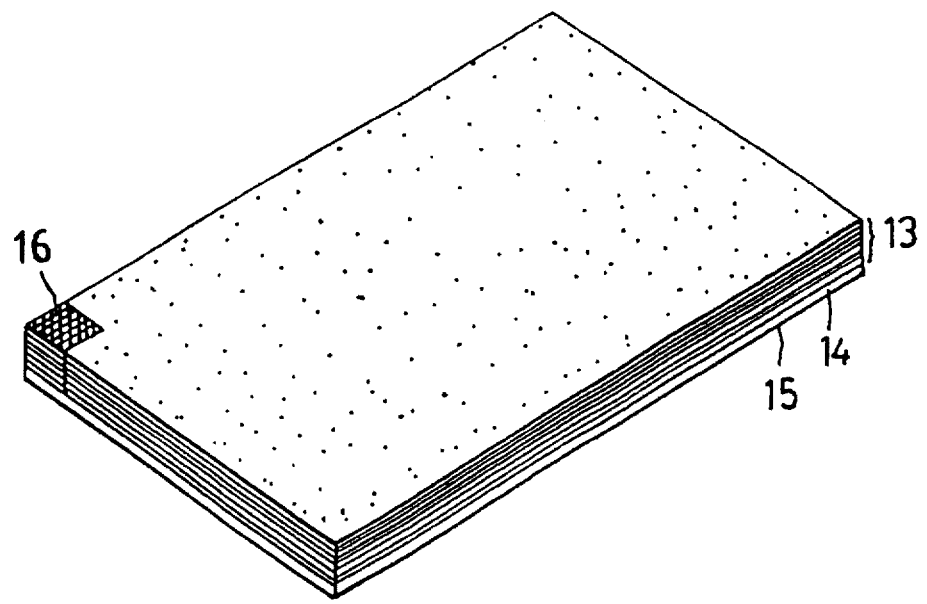
FIG. 6 is a perspective view showing a laminate used in the microbicidal mat shown in FIG. 5.

FIGS. 5 and 6 are each a perspective view showing a microbicidal mat adopted as another embodiment of the present invention. This mat includes a mat body 11 having a waterstop film 12 laminated on the underside thereof for stopping water, like the foregoing embodiment. The mat body 11 is composed of a fiber material or a foamed polymer resin which are capable of being impregnated with a microbicide or a disinfectant.

The waterstop film 12 may comprise polyethylene, polypropylene, nylon, polyester or the like, and its thickness is adequately about 10 to about 100 μm. The waterstop film 12 serves to stop a solution of a disinfectant or microbicide impregnating the mat body 11 when used.

The mat body 11 may preliminarily contain a chemical agent which serves as a microbicide or a disinfectant when mixed with water or may be impregnated with a chemical solution containing a microbicide or a disinfectant by spraying the chemical solution upon.

The mat body 11 laminated with the waterstop film 12 on the underside thereof rests on a laminate of a multiplicity of release films 13. This laminate comprises a lamination of a multiplicity of release films each coated with a sticky material on the top surface thereof, as shown in FIG. 6. Each of the release films 13 is provided at one corner thereof with a label-like portion 13 for stripping off the release film 13 so as to allow the laminated release films 13 to be stripped off one by one from this portion.

The underside of the lowermost layer of this laminate is applied with a sticky material and is bonded to a thick sheet 14 as shown in FIG. 6. Further, this thick sheet is provided with a release paper 15 on the underside thereof.

In use, the release paper 15 is stripped off to expose the thick sheet 14 and then the laminate is bonded to the floor adjacent the entrance of a clean zone. Thereafter, the mat body 11 with its waterstop film 12 oriented downward is placed on the release film 13 of the laminate. Since the top surface of the release film 13 of the laminate is coated with the sticky material, the mat body 11 is fixed on the laminate through the waterstop film 12.

Subsequently, the mat body 11 is impregnated with a chemical solution containing a microbicide or a disinfectant by supplying the chemical liquid thereto. Where the mat body 11 preliminarily contains such an agent in a crystallized state as in the foregoing embodiment, it is only required that the mat body 11 be sprayed with water. When the surface of the mat body 11 becomes dirty one to several days after the beginning of use, the release film 13 together with the mat body 11 should be stripped off from the label-like portion 16 of the laminate and then subjected to disposal such as by incineration. New mat body 11 is in turn placed on the next release film 13 of the laminate, and the foregoing procedure is repeated.

Figure 7:
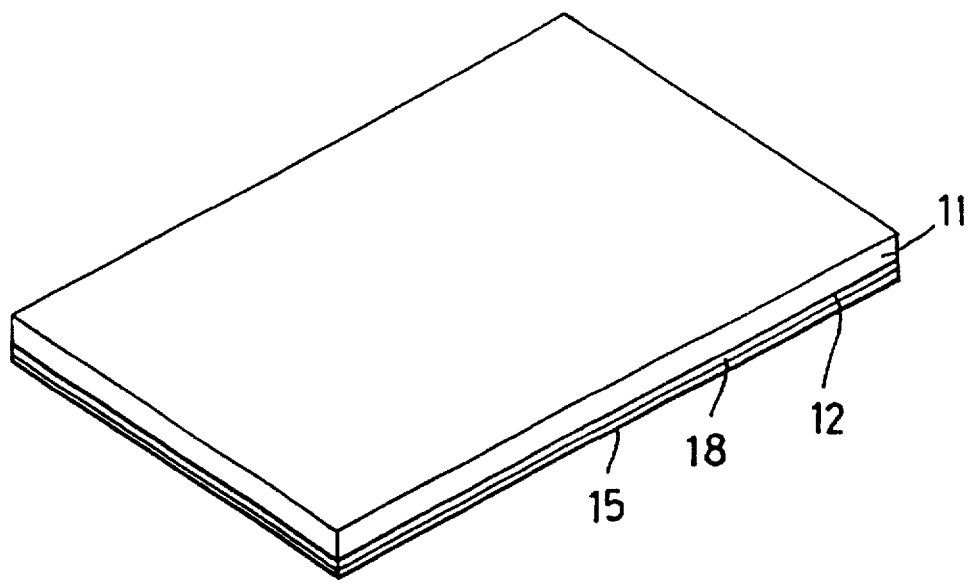
FIG. 7 is a perspective view showing yet another embodiment of the frameless microbicidal mat.

FIG. 7 is a perspective view of a microbicidal mat employed as yet another embodiment of the invention. This microbicidal mat comprises mat body 11 placed on a thermo-plastic elastomer sheet having stickiness on the surface thereof. The elastomer sheet 18 having stickiness on the surface thereof can be washed with water to wash away dust and soil attached to the surface thereof and recover its stickiness after washing; therefore, it possesses a property enabling repeated use.

According to this embodiment, the elastomer sheet 18 is installed at a given location, and the mat body 11 is placed thereon. The mat body 11 is bonded to the elastomer sheet 18 by means of the stickiness of the sheet 18. The mat body 11 is caused to take effect by directly impregnating the mat body 11 with a chemical solution or by supplying water to the mat body 11. After a predetermined period of use, only the mat body 11 should be stripped off from the elastomer sheet 18 and then subjected to disposal such as by incineration. Since the elastomer sheet 18 will maintain the stickiness of its surface even after the used mat body 11 has been stripped off, the elastomer sheet 18 can be repeatedly used by placing new mat body 11 thereon.

The following are experimental examples of microbicidal mats according to the embodiments shown in FIGS. 5 to 7.

EXPERIMENTAL EXAMPLE 1

Thirty polyethylene films 13 each having a thickness of 50 μm and coated with an acrylic sticky material as shown in FIG. 2 were stacked one on another to form a laminate, which was in turn bonded securely to the top surface of a polyester sheet 14 that was as thick as 100 μm and was coated with an acrylic sticky material on opposite sides thereof. The under-side of the polyester sheet 14 was covered with a release paper 15 applied with silicone coat. Onto the mat thus formed having a size of 600 mm×1200 mm (tradename "DKI MAT" produced by Daiken Iki Co., Ltd.) was securely bonded a mat body 11 comprising a dry nonwoven fabric of 100% rayon having a size of 600 mm×1000 mm and a METSUKE of 150 g/m² and a polyester film 12 of 30 μm thickness laminated on the under-side of the fabric, thus forming a microbicidal mat. The dry nonwoven fabric had been preliminarily impregnated with a 3% solution of alkylpolyaminoethylglycine as a disinfectant and then dried.

This microbicidal mat with the release paper 15 stripped off therefrom was placed at the entry of an operating room of a hospital and sprayed with water. Since the mat became conspicuously soiled after used for a week, a release film 13 of the laminate together with the mat body 11 was stripped off from the label-like portion 16 and subjected to disposal. A new mat body 11 was then securely bonded to the next release film 13 of the laminate. This procedure was repeated. In this case the mat body 11 was able to be readily stripped off together with release film 13, and thus the replacement operation could be easily carried out without any problem.

EXPERIMENTAL EXAMPLE 2

A cellulose sponge of 3 mm thickness (tradename "CHAFFLOSE SPONGE" available from CHAFFLOSE CORPORATION) was laminated with a polyester film 12 (thickness: 50 μm) and impregnated with a 5% benzalkonium chloride solution, then dried. The resultant was cut to a size of 500 mm×1000 mm to form a mat body 11.

On the other hand, a 1 mm-thick polyurethane elastomer 8 (tradename: "TG SHEET" available from MOCHIDA SHOKO CO.) having stickiness on opposite sides thereof and covered with a polyester film on each side was cut to a size of 500 mm×1000 mm. The polyester film on top of the resultant elastomer 8 was stripped off and then the mat body 11 was securely bonded onto the elastomer 8.

In the same manner as in Experimental Example 1, the microbicidal mat thus formed was installed in a hospital with the film on the underside thereof being stripped off. Ten days thereafter, the mat body 11 was stripped off from the polyurethane elastomer 8 together with the waterstop film 12 and then subjected to disposal. New mat body 11 was then securely bonded onto the same elastomer 8. This procedure was repeated with facilitated stripping-off operation and satisfactory handling properties.

INDUSTRIAL APPLICABILITY

Microbicidal mats according to the present invention can be used in preventing various microbes from being brought into clean zones of semiconductor plants, biochemical plants, hospitals, old-aged homes or like facilities by persons entering the clean zones.

We claim:

1. A microbicidal mat to be installed at an entrance of a clean zone comprising a liquid-absorptive mat body, and an alkaline compound contained therein as a microbicide, wherein the mat body and the alkaline compound are not substantially chemically bonded to each other.

2. A microbicidal mat as set forth in claim 1, wherein the mat body further contains a surface active agent.

3. A microbicidal mat as set forth in claim 1 wherein the mat body further contains a water-retentive agent comprising a substance which is stable against water and has deliquescence.

4. A microbicidal mat as set forth in claim 1 wherein any of the substances contained in the mat body are in a powdery state before the mat is installed at the entrance of the clean zone.

5. A microbicidal mat as set forth in claim 4, wherein any of the substances contained in the mat body are in the form of a powdery crystal resulting from its recrystallization in the mat body.

6. A microbicidal mat as set forth in claim 1 wherein the alkaline compound is a compound selected from the group consisting of an alkali metal carbonate, an alkali metal bicarbonate, an alkali metal borate, and an alkali metal phosphate.

7. A microbicidal mat as set forth in claim 2 wherein the surface active agent comprises an anionic surface active agent.

8. A microbicidal mat as set forth in claim 1 wherein the mat body comprises a combustible nonwoven fabric.

9. A microbicidal mat as set forth in claim 8, wherein the mat body is provided on a top surface thereof with fuzzing-preventive portions made of a resin in a scattered fashion.

10. A microbicidal mat as set forth in claim 1 wherein the mat body comprises a foamed polymer resin.

11. A microbicidal mat as set forth in claim 1 wherein the mat body is laminated with a waterstop film on the underside thereof.

12. A microbicidal mat as set forth in claim 11, wherein the waterstop film is provided with a sticky layer on the underside thereof.

13. A microbicidal mat as set forth in claim 11, wherein a laminate comprising a plurality of stacked release films each coated with a sticky material on opposite sides thereof is provided on the underside of the waterstop film.

14. A microbicidal mat as set forth in claim 13, wherein the laminate is provided with a sticky layer on the underside thereof.

15. A microbicidal mat as set forth in claim 11, wherein a thermoplastic elastomer sheet having stickiness on a surface thereof is provided on the underside of the waterstop film.

16. A microbicidal mat as set forth in claim 8 wherein the mat body is fitted in a recess of a frame.

17. A microbicidal mat as set forth in claim 8 wherein the mat body has a bank portion formed of a hydrophobic synthetic resin and enclosing the outer peripheral edges thereof.

18. A method of manufacturing a microbicidal mat to be installed at an entrance of a clean zone, comprising a first step of impregnating a mat body with an aqueous solution of an alkaline compound serving as a microbicide, and a second step of drying the mat body to cause the alkaline compound to recrystallize in the mat body.

19. A method as set forth in claim 18, wherein:

in the first step the aqueous solution further contains, as dissolved therein, a surface active agent and/or a water-retentive agent, the water-retentive agent comprising a substance which is stable against water and has deliquescence; and in the second step the surface active agent and/or the water-retentive agent are caused to recrystallize together with the alkaline compound.

20. A method of using a microbicidal mat to be installed at an entrance of a clean zone, comprising the steps of:

providing a mat body containing an alkaline compound serving as a microbicide, the alkaline compound being in a crystalline state in the mat body; and supplying the mat body with water in an amount such as to attain a pH value of from 9 to 12 and using the mat with the mat body in a wet state.

21. A method as set forth in claim 20, wherein the mat body further contains therein a surface active agent in a crystalline state before the mat body is supplied with water, and the amount of the surface active agent is such that when the mat body is supplied with water in an amount such as to attain a pH value of from 9 to 12, the concentration of the surface active agent is from 0.1 to 0.5 vol. %.

22. A method as set forth in claim 20 wherein the mat body further contains a water-retentive agent comprising a substance which is stable against water and has deliquescence, the water-retentive agent being in a crystalline state in the mat body before the mat body is supplied with water.

* * * * *